United States Patent [19]

Plagens

[11] Patent Number: 4,698,524

[45] Date of Patent: Oct. 6, 1987

[54] MESFET LOGIC USING INTEGRAL DIODE LEVEL SHIFTING

[75] Inventor: Mark R. Plagens, Richardson, Tex.

[73] Assignee: Honeywell Inc., Minneapolis, Minn.

[21] Appl. No.: 886,596

[22] Filed: Jul. 16, 1986

[51] Int. Cl.[4] ............... H03K 19/094; H03K 19/092; H03K 19/02
[52] U.S. Cl. .................................. 307/450; 307/475; 307/446
[58] Field of Search ............... 307/443, 445, 446, 448, 307/475, 264, 571, 450, 458

[56] References Cited

U.S. PATENT DOCUMENTS

| 4,400,636 | 8/1983 | Andrade | 307/446 |
| 4,404,480 | 9/1983 | Ransom et al. | 307/475 |
| 4,410,815 | 10/1983 | Ransom et al. | 307/448 |
| 4,558,235 | 12/1985 | White et al. | 307/443 |

FOREIGN PATENT DOCUMENTS

| 0075915 | 4/1983 | European Pat. Off. | 307/450 |
| 0019033 | 2/1983 | Japan | 307/446 |
| 0953733 | 8/1982 | U.S.S.R. | 307/446 |

OTHER PUBLICATIONS

Livingstone, "Capacitor Coupling of GaAs Depletion Mode F.E.T.S", IEE Proc, vol. 127, pt. 1, No. 5, Oct. 1980.

Freeman, "Level Shifting Circuit", IBM Technical Disclosure Bulletin, vol. 18, No. 5, Oct. 1975.

Primary Examiner—Stanley D. Miller
Assistant Examiner—Trong Quang Phan
Attorney, Agent, or Firm—Charles L. Rubow

[57] ABSTRACT

A semiconductor logic circuit utilizing level shifting of input transistors away from a reference voltage level but shifting the output toward the reference voltage level to increase noise margin. The input signals may switch both the input transistors and the output transistors.

7 Claims, 2 Drawing Figures

MESFET LOGIC USING INTEGRAL DIODE LEVEL SHIFTING

The present invention relates to semiconductor logic circuits, and more particularly to such circuits using diodes to provide integral level shifting.

BACKGROUND OF THE INVENTION

A problem which arises in the development of semiconductor digital integrated circuits, relates to the noise margin of the individual gates in such a circuit. As more gates are added to such circuits the cumulative noise of the gates may rapidly exceed the available noise margin. This problem is compounded when a circuit must be able to operate over a wide temperature range, such as the military temperature range of −55° C. to +125° C. Problems related to such limited noise margins have been largely overcome in the area of silicon integrated circuits, but still are significant in circuits based on gallium arsenide or other more recently developed semiconductor materials. Thus a semiconductor logic family having improved noise margins would be very useful in allowing such newer semiconductor materials extended temperature operating range, and permitting a higher level of integration.

SUMMARY OF THE INVENTION

The present invention utilizes level shifting means to shift the switchpoint of the switching transistors in a logic gate further from ground potential. By thus moving the switchpoint of the transistors away from ground potential a higher voltage is required to switch the transistors from the on state to the off state or vice versa. Thus there is a larger range between the system low voltage level, or logic "0" and the switchpoint above which the signal will be interpreted as the system high voltage level or logic "1". In the preferred embodiment the level shifting means includes Schottky diodes.

DETAILED DESCRIPTION OF PREFERRED EMBODIMENTS

Figure 1:
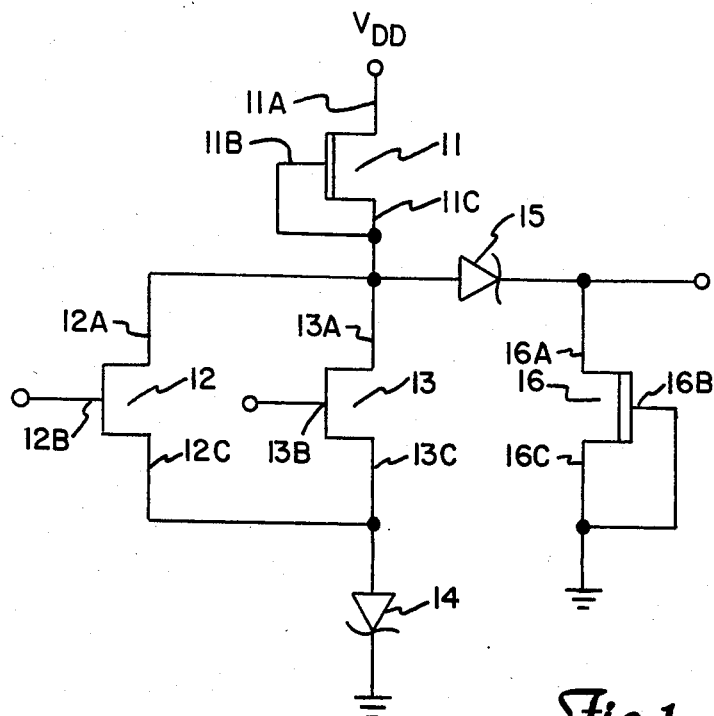
FIG. 1 is a diagram of a two input NOR gate according to the invention.

FIG. 1 illustrates a two input NOR gate according to the invention. The circuit of FIG. 1 includes a depletion mode field effect transistor 11 (FET) which has a drain terminal 11A which is designed to be electrically connected to the system $V_{DD}$, a gate terminal 11B, and a source terminal 11C. Gate terminal 11B and source terminal 11C are electrically connected to one another, so that transistor 11 will function as a current source. Source 11C of transistor 11 is electrically connected to drain 12A of transistor 12 and 13A of transistor 13. Input signals to the gate are provided to gates 12B and 13B of transistors 12 and 13 respectively. Sources 12C and 13C of transistors 12 and 13 respectively are electrically connected to one another and to level shifting diode 14. Level shifting diode 14 is in turn electrically connected to a source of electrical ground potential.

Source 11C of transistor 11 is further electrically connected to level shifting diode 15. Level shifting diode 15 is electrically connected to the system output and to drain 16A of transistor 16. Gate 16B and source 16C of transistor 16 are electrically connected to one another and to a source of electrical ground potential.

The function of diode 14 in the circuit of FIG. 1 is to shift the switching level of transistors 12 and 13 to a voltage farther from ground potential than would be the case if diode 14 were not present. In so doing the switchpoint of the transistors, and hence the voltage level which is detected as a system high voltage signal is moved away from the nominal system low voltage level. Thus a greater noise margin is provided, i.e. the system is able to tolerate greater electrical noise while still functioning properly.

Level shifting diode 15 and transistor 16 provide output level shifting to insure that the output low voltage remains at or near ground potential, in order to allow subsequent gates to correctly interpret the output signals from the gate of FIG. 1.

Figure 2:
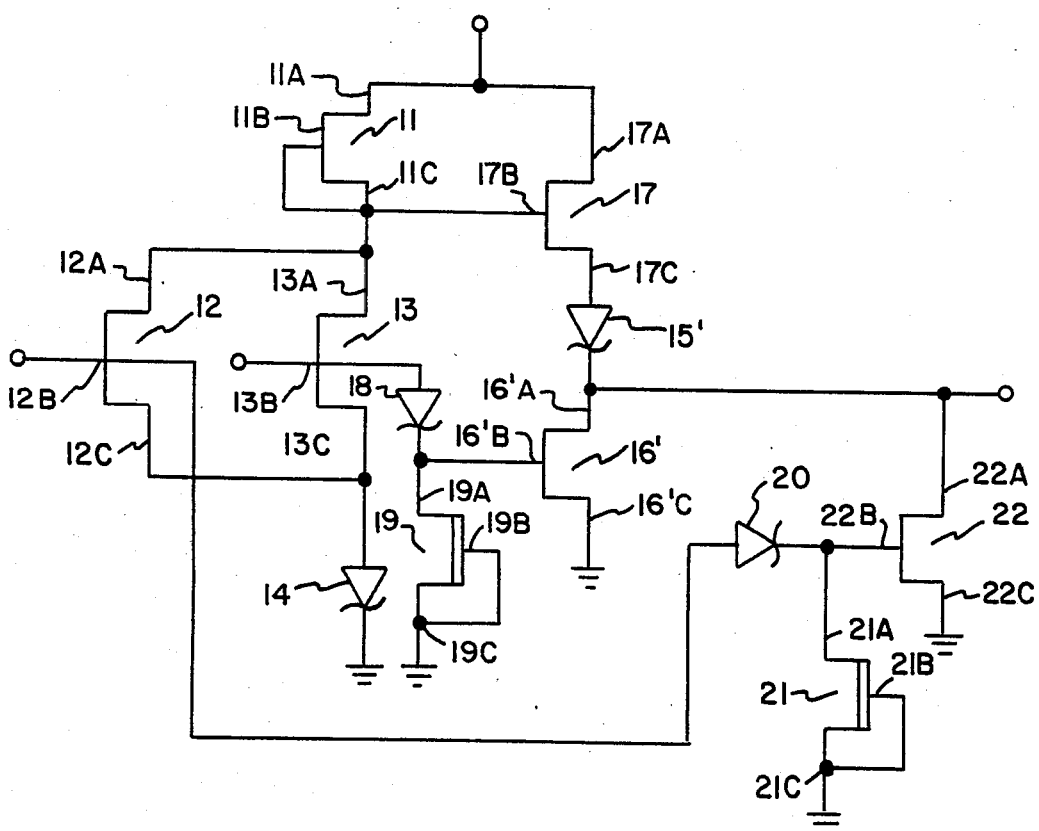
FIG. 2 is a drawing of a two input NOR gate including an output buffer state for a stronger output signal.

FIG. 2 shows a second gate according to the invention. In the gate of FIG. 2, however, an output stage has been added to provide greater output drive. This acts as an amplifier to allow the circuit to drive more subsequent gates than would be possible with the circuit of FIG. 1, or to operate better if the system is to drive a transmission line having a larger capacitance. In the circuit of FIG. 2 transistor 11 functions as did transistor 11 of FIG. 1. Transistors 12 and 13 are connected similarly to the corresponding transistors of FIG. 1 except that level shifting diode 15' is electrically connected to source region 17C of transistor 17 rather than source region 11A of transistor 11.

The output stage further includes diode 18 and transistor 19. These devices shift the input signal level to a transistor 16' such that it is switched at the same voltage as transistor 13 for push-pull operation.

Gate region 12B of transistor 12 is further electrically connected to diode 20 which is in turn electrically connected to drain region 21A of transistor 21. Gate region 21B of transistor 21 is electrically connected to source region 21C which is electrically connected to a source of electrical ground. Those skilled in the art will readily perceive that diode 20 and transistor 21 provide a function for inputs to transistor 22 similar to the function provided by diode 18, and transistor 19 for inputs to transistor 16'. Diodes 18 and 20 are electrically connected to gate regions 16'B and 22B of transistors 16' and 22 respectively. Source regions 19C and 22C of transistors 19 and 22 are electrically connected to a source of electrical ground potential while drain regions 16'A and 22A of transistors 19 and 22 respectively are electrically connected to one another and to the gate output. The circuit of FIG. 2 will provide similar advantages to that of FIG. 1 with the additional advantage of providing an enhanced output signal.

In the preferred embodiments of the invention all FETs in the circuit are metal semiconductor field effect transistors (MESFETs). Those skilled in the art will readily perceive, however, that the invention is not limited to MESFETs. Other type of transistors, such as insulated gate field effect transistors could be utilized. Those skilled in the art will further perceive that other output stages could be effectively utilized, depending upon the requirements in a particular application.

The embodiments of the invention in which an exclusive property or right is claimed are defined as follows:

1. A semiconductor logic circuit comprising:
   a first field effect transistor means having a drain terminal means, a gate terminal means, and a source terminal means, said first field effect transistor means drain terminal means being for electrical connection to a first voltage source and said first field effect transistor means gate terminal means being electrically connected to said first field effect transistor means source terminal means;

a second field effect transistor means having a drain terminal means, a gate terminal means, and a source terminal means, said second field effect transistor means drain terminal means being electrically connected to said first field effect transistor means source terminal means and said second field effect transistor means gate terminal means being for receiving input signals;

a first threshold device means having first and second terminal means between which current substantially flows only if any voltage occurring therebetween exceeds a threshold, said first threshold device means first terminal means being electrically connected to said second field effect transistor means source terminal means, said first threshold device means second terminal means being for electrical connection to a second voltage source;

a third field effect transistor means having a drain terminal means, a gate terminal means, and a source terminal means, said third field effect transistor means drain terminal means being for electrical connection to a third voltage source and said third field effect transistor means gate terminal means being electrically connected to said first field effect transistor means source terminal means;

a second threshold device means having first and second terminal means between which current substantially flows only if any voltage occurring therebetween exceeds a threshold, said second threshold device means first terminal means being electrically connected to said third field effect transistor means source means, said second threshold device means second terminal means being for providing output signals;

a fourth field effect transistor means having a drain terminal means, a gate terminal means, and a source terminal means, said fourth field effect transistor means drain terminal means being electrically connected to said second threshold device means second terminal means, said fourth field effect transistor means source terminal means being for electrical connection to a fourth voltage source;

a third threshold device means having first and second terminal means between which current substantially flows only if any voltage occurring therebetween exceeds a threshold, said third threshold device means first terminal means being electrically connected to said second field effect transistor means gate terminal means, and said third threshold device means second terminal means being electrically connected to said fourth field effect transistor means gate terminal means; and a fifth field effect transistor means having a drain terminal means, a gate terminal means, and a source terminal means, said fifth field effect transistor means drain terminal means being electrically connected to said fourth field effect transistor means gate terminal means, said fifth field effect transistor means source terminal means being for electrical connection to a fifth voltage source, and said fifth field effect transistor means gate terminal means being electrically connected to said fifth field effect transistor means source terminal means.

2. The apparatus of claim 1 where, in addition to said second field effect transistor means, there is a further first plurality of field effect transistor means for receiving input signals each having a drain terminal means, a gate terminal means, and a source terminal means, each said drain terminal being electrically connected to said first field effect transistor means source terminal means and each source terminal means in said first plurality of field effect transistor means being electrically connected to said first threshold device means first terminal means, and each of said gate terminal means in said first plurality of field effect transistor means being for receiving input signals.

3. The apparatus of claim 1 wherein said first, second and third threshold device means are each diode means with an anode terminal means serving as first terminal means thereof and a cathode terminal means serving as a second terminal means thereof.

4. The apparatus of claim 2 which further comprises a plurality of threshold device means, in addition to said third threshold device means for receiving input signals, each of said threshold device means in said plurality thereof having first and second terminal means between which current substantially flows only if any voltage therebetween exceeds a threshold, each of said first terminal means of said plurality of threshold means being electrically connected to a corresponding one of said gate terminal means of said first plurality of field effect transistor means, and further comprising a second plurality of field effect transistor means each having a drain terminal means, a gate terminal means, and a source terminal means, each said drain terminal means of one of said second plurality of field effect transistor means being electrically connected to a corresponding one of said second terminal means of said plurality of threshold device means, each of said source terminal means of said second plurality of field effect transistor means being for electrical connection to said third voltage source, and each of said second terminal means of said plurality of threshold devices being electrically connected to a corresponding one of said gate terminal means of said second plurality of said field effect transistor means.

5. The apparatus of claim 3 wherein said first voltage source and said third voltage source are a common voltage source, and wherein said second voltage source, said fourth voltage source, and said fifth voltage source are a common voltage source.

6. The apparatus of claim 4 where said first, second and third threshold devices and each of said plurality of threshold device means are each diode means each having an anode means serving as said first terminal means and a cathode means serving as said second terminal means.

7. The apparatus of claim 6 wherein said first voltage source and said third voltage source are a common voltage source, and wherein said second voltage source, said fourth voltage source, and said fifth voltage source are a common voltage source.

* * * * *

UNITED STATES PATENT AND TRADEMARK OFFICE
CERTIFICATE OF CORRECTION

PATENT NO. : 4,698,524

DATED : OCTOBER 6, 1987

INVENTOR(S) : MARK R. PLAGENS

It is certified that error appears in the above-identified patent and that said Letters Patent is hereby corrected as shown below:

Claim 2, line 6, after "terminal" insert --means in said plurality of said field effect transistor means--.

Signed and Sealed this

Twenty-sixth Day of January, 1988

Attest:

DONALD J. QUIGG

*Attesting Officer*   *Commissioner of Patents and Trademarks*